US00PP30980P2

(12) United States Plant Patent
Moore

(10) Patent No.: US PP30,980 P2
(45) Date of Patent: Oct. 29, 2019

(54) RASPBERRY PLANT NAMED 'WSU 2166'

(50) Latin Name: ***Rubus idaeus* L.**
Varietal Denomination: WSU 2166

(71) Applicant: Washington State University, Pullman, WA (US)

(72) Inventor: Patrick Peder Moore, Puyallup, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 15/932,804

(22) Filed: Apr. 27, 2018

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Christensen O'Connor Johnson Kindness PLLC

(57) ABSTRACT

This invention relates to a new and distinct variety of red raspberry plant (*Rubus idaeus* L.) named 'WSU 2166' adapted to the raspberry production area of the Pacific Northwest. 'WSU 2166' is primarily characterized by suitability for machine harvestability, tolerance to root rot, early season production and large, conical fruit that is longer than it is broad.

6 Drawing Sheets

STATEMENT REGARDING FEDERALLY-SPONSORED RESEARCH

This invention was made with government support under Grant No. 2012-31100-06053, awarded by United States Department of Agriculture through the National Institute of Food and Agriculture, and under Grant No. 58-5358-9-440, awarded by United States Department of Agriculture through the Agricultural Research Service. The government has certain rights in the invention.

Latin name: This invention concerns a new and distinct cultivar of red raspberry plant with a botanical name of *Rubus idaeus* L.

Varietal denomination: The varietal denomination of the claimed raspberry is 'WSU 2166'.

FIELD OF THE INVENTION

This invention concerns a new and distinct cultivar of red raspberry plant with a botanical name of *Rubus idaeus* L. The intended market use for the fruit is as fresh or frozen.

BACKGROUND

Raspberries are an economically important crop in the United States and many cultivars of raspberry plant are known. However, there is a need to develop new raspberry varieties with improved characteristics.

The present invention relates to a new and distinct floricane bearing (summer fruiting on second year canes) red raspberry variety designated as 'WSU 2166'. The variety is botanically known as *Rubus idaeus* L. The new and distinct variety of red raspberry originated from a hand-pollinated cross of Washington State University selection 1447 (unpatented) as the maternal parent and Washington State University selection 0697 (unpatented) as the paternal parent.

The cross was made in Year 1 at Puyallup, Wash. Seeds were germinated in the winter of Year 1-2 and the resulting seedlings planted in Year 2 with a cooperating raspberry grower in Burlington, Wash. Selections were made in Year 4, while riding a raspberry harvester.

Varietal designation 'WSU 2166' was selected in Year 4 and asexually propagated at Puyallup, Wash. by tissue culture using meristem cultures from axillary buds of primocanes. This selection was planted in non-replicated plots with a cooperating grower in Year 5 and planted with a second grower in Year 8. The plantings were maintained by the growers using typical commercial methods and fruit machine harvested. The plantings were subjectively evaluated weekly for adaptation to machine harvesting for two fruiting seasons. In all harvest seasons this selection machine harvested well and had large fruit size. This selection was tested for tolerance to root rot. Plants and fruit of this new variety have remained true to type through successive generations of asexual propagation. The raspberry plant that is the subject of this disclosure is being named and released as 'WSU 2166'.

SUMMARY

The following traits have been repeatedly observed and are determined to be unique characteristics of 'WSU 2166', which in combination distinguish this raspberry plant as a new and distinct variety:

1. Large fruit size
2. Conic fruit shape, with fruit longer than broad
3. Tolerance to root rot
4. Suitability for machine harvesting 'WSU 2166' is distinguished from its maternal parent, Washington State University selection 1447, by larger fruit and softer fruit.

'WSU 2166' is distinguished from its paternal parent, Washington State University selection 0697, by larger fruit, a greater fruit length to width ratio, and firmer fruit.

'WSU 2166' is distinguished from 'Cascade Harvest' (U.S. Plant Pat. No. 26,369), by earlier fruiting, firmer fruit, darker fruit and greater tolerance to root rot.

'WSU 2166' is distinguished from the most commonly grown red raspberry in the Pacific Northwest, 'Meeker' (unpatented), by larger fruit, firmer fruit, earlier fruiting, more drupelets per fruit, greater fruit length to width ratio and greater tolerance to root rot.

'WSU 2166' is distinguished from 'Willamette' (unpatented) by larger fruit, greater fruit length to width ratio, lighter colored fruit and greater tolerance to root rot.

DESCRIPTION OF THE DRAWINGS

The accompanying photographs illustrate typical characteristics of the new variety 'WSU 2166' and are true to color as it is reasonably possible with color reproductions of this type. Color in the photographs may differ slightly from the color value cited in the detailed botanical description, which accurately describes the color of 'WSU 2166'. When objects could be accurately measured with an 8 mm diameter measuring opening (leaves, fruit and some canes), color was measured with a Minolta CR-400 Colorimeter, which measures color in L*, a*, b* color coordinates. Calibration was performed using a standard white plate supplied by the manufacturer. The Minolta CR-400 Colorimeter (CIE2000) expressed the data in Munsell notation. For other color measurements, color was compared with Royal Horticultural Society Colour Chart (R.H.S.) color plates and presented using Royal Horticultural Society Colour Chart Second Edition (1966) designations. Petal color was determined using R.H.S. Colour Chart Sixth edition (2015).

DETAILED BOTANICAL DESCRIPTION

Figure 1:
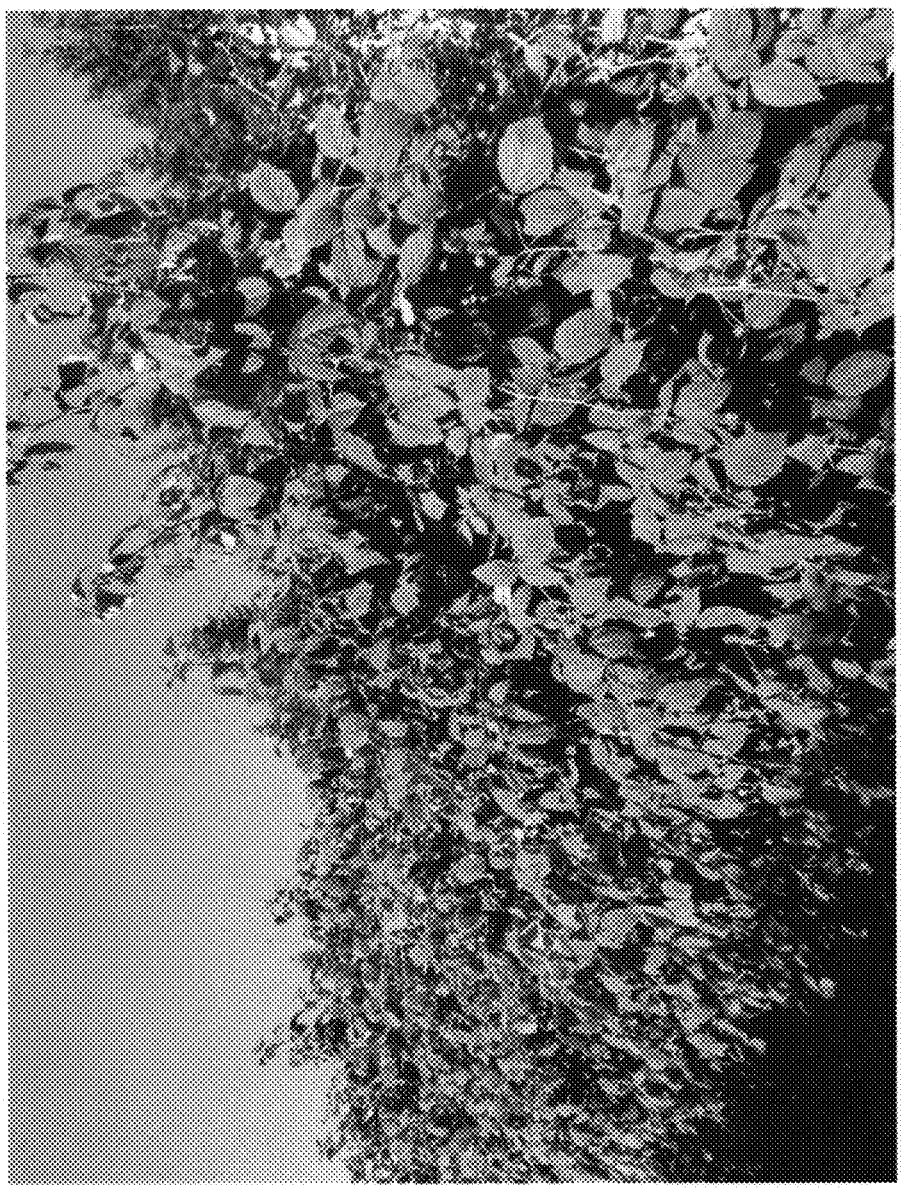
FIG. 1 is a picture of the plant of 'WSU 2166', showing the growth habit of the plant and display of the fruit on 6 Jul. 2011, Lynden, Wash.
Figure 2:
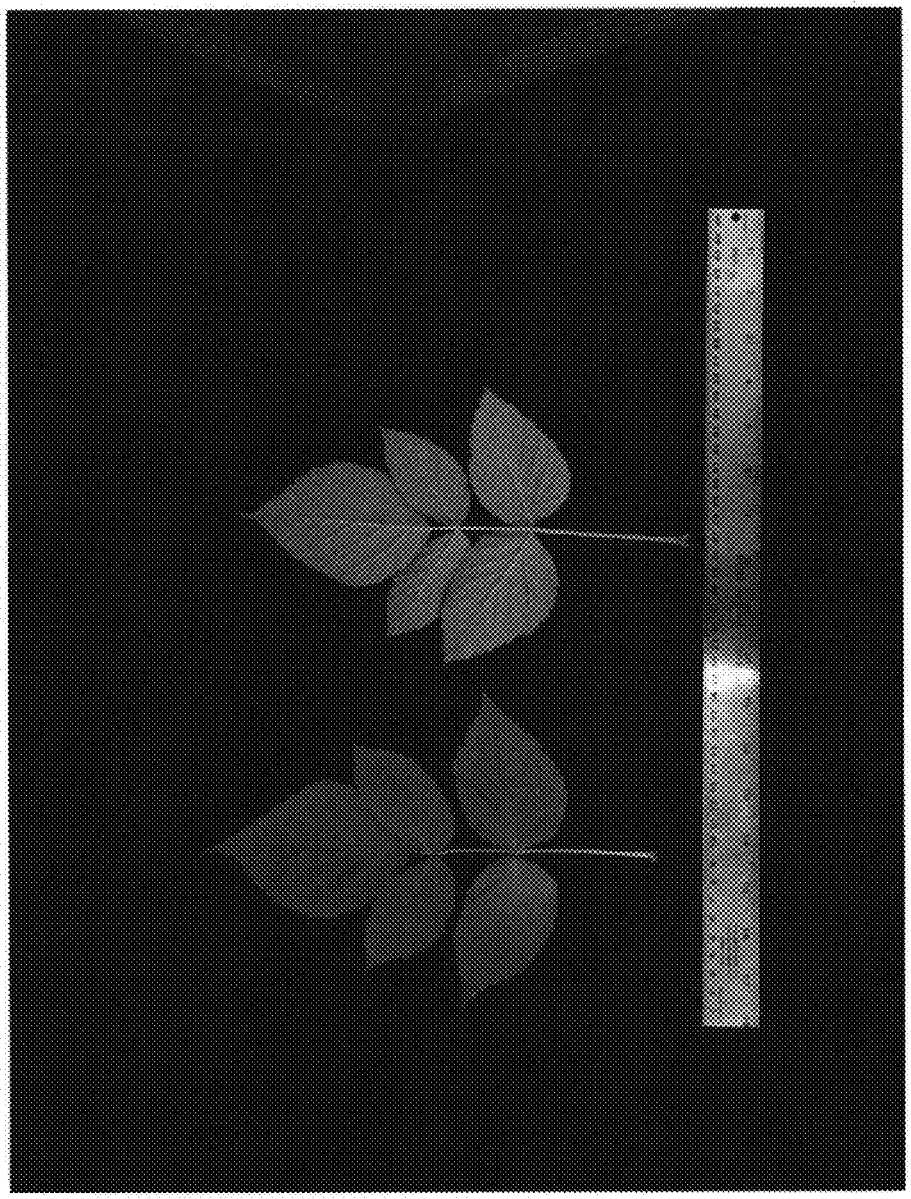
FIG. 2 is a photograph of primocane leaves of 'WSU 2166' on 20 Jun. 2011, Puyallup, Wash..
Figure 3:
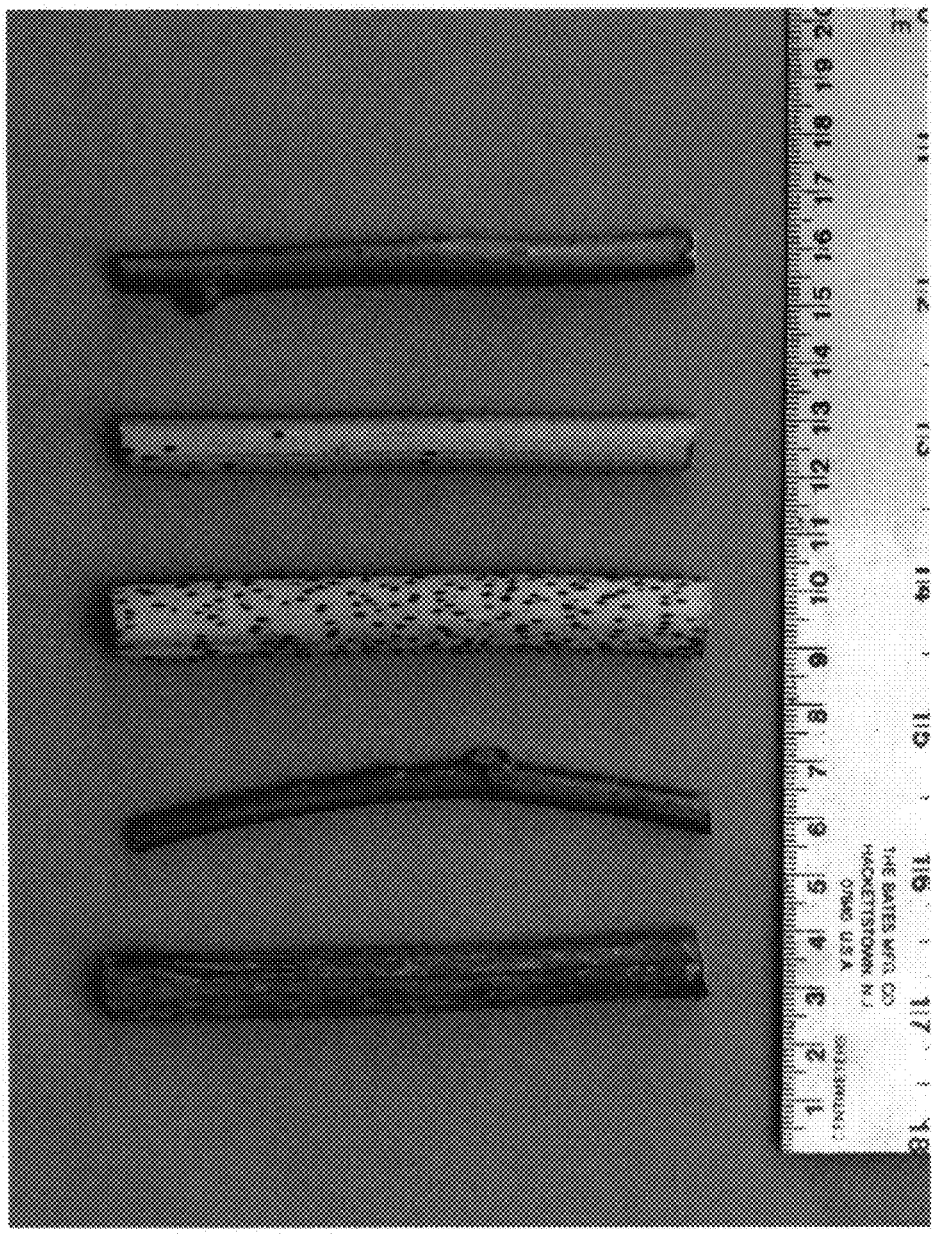
FIG. 3 is a photograph of cane segments, from left to right: basal segment of floricane, segment of the mid-section of floricane, basal segment of primocane, mid-section of primocane and upper section of primocane of 'WSU 2166' taken 1 Sep. 2011, Puyallup, Wash. showing the frequency and shape of the spines and spine base.
Figure 4:
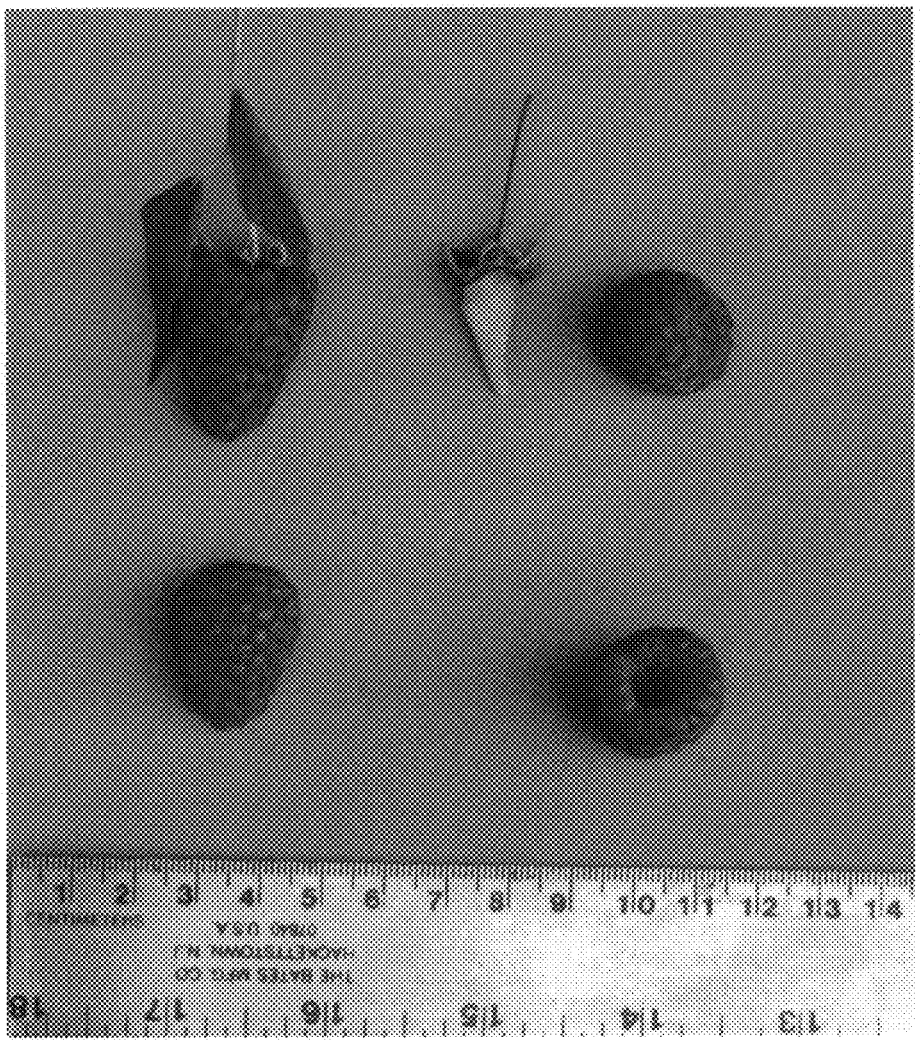
FIG. 4 is a photograph of fruit and receptacle of 'WSU 2166' taken 7 Jul. 2011, Puyallup, Wash.
Figure 5:
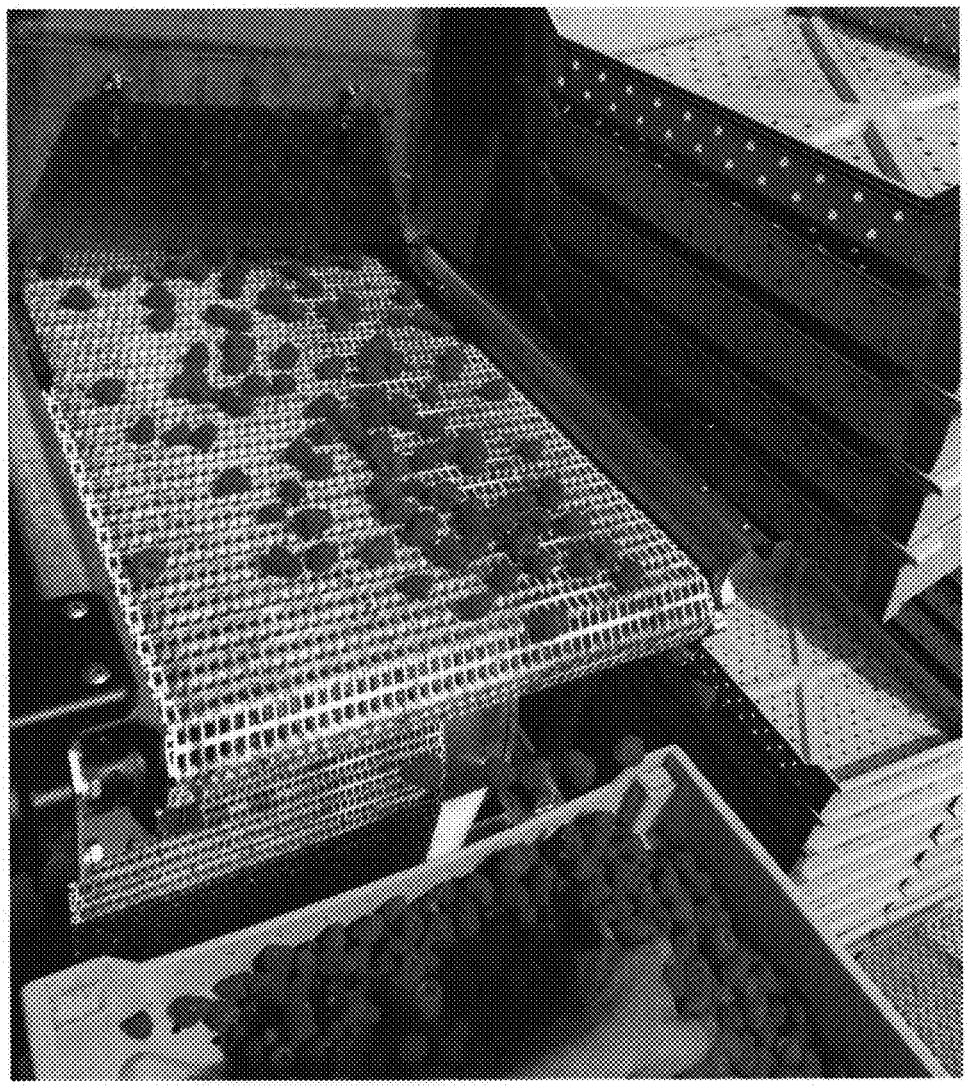
FIG. 5 is a photograph of machine harvested fruit of 'WSU 2166' taken 30 Jun. 2010, Lynden, Wash.
Figure 6:
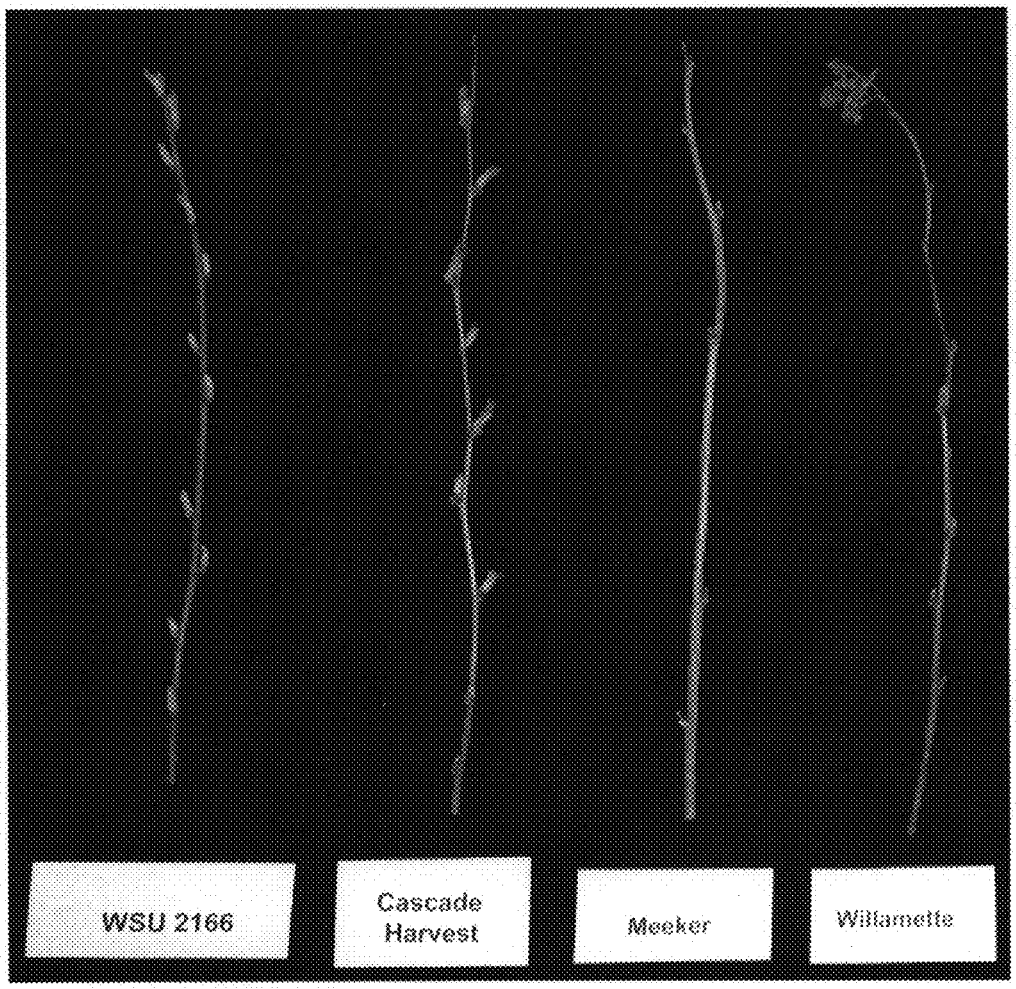
FIG. 6 is a photograph showing spring bud development of 'WSU 2166' relative to commonly grown cultivars taken 21 Feb. 2012, Puyallup, Wash. Bud development of 'WSU 2166' was slightly slower than 'Cascade Harvest' but more developed than 'Meeker' and 'Willamette'

'WSU 2166' has not been observed under all possible environmental conditions and as such the characteristics may vary in detail depending on weather conditions, day length, soil type and location. The description is based on observations taken in Year 11 (except as noted) at Puyallup, Wash. and with cooperating growers in Lynden, Wash.

A comparison of fruit of 'WSU 2166' with cultivars commonly grown in Washington is given in Table 1. 'WSU 2166' had similar machine harvest yield as 'Meeker' and 'Willamette' and slightly less yield than for 'Cascade Harvest'. 'WSU 2166' had earlier midpoints of harvest than 'Cascade Harvest' and 'Meeker'. In the Puyallup planting, 'WSU 2166' had lower yield in Year 10 than the other cultivars, but had yield comparable to the other cultivars in Year 11. 'WSU 2166' had the largest fruit weight, firmest fruit, lowest fruit rot, and was earlier than 'Cascade Harvest' and 'Meeker'. The lower fruit rot may be partially a result of the weather for the 'WSU 2166' harvest season.

TABLE 1

| Harvest data | | | | |
|---|---|---|---|---|
| | 'WSU 2166' | 'Cascade Harvest' | 'Meeker' | 'Willamette' |
| Machine harvest, Lynden, WA[Z] | | | | |
| Yield (t/a) | | | | |
| Year 10 | 8.1 | 9.3 | 6.1 | 6.4 |
| Year 11 | 5.8 | 7.5 | 7.3 | 5.8 |
| Total | 13.9 | 16.8 | 13.4 | 12.2 |
| Date of first harvest | | | | |
| Year 10 | 6/13 | 6/17 | 6/20 | 6/13 |
| Year 11 | 6/30 | 7/4 | 7/7 | 7/1 |
| Midpoint of harvest | | | | |
| Year 10 | 6/23 | 7/1 | 7/3 | 6/22 |
| Year 11 | 7/11 | 7/17 | 7/19 | 7/12 |
| Date of last harvest | | | | |
| Year 10 | 7/6 | 7/13 | 7/14 | 7/6 |
| Year 11 | 7/21 | 7/27 | 7/27 | 7/20 |
| Hand harvest, Puyallup, WA[Y] | | | | |
| Yield (t/a) | | | | |
| Year 10 | 3.7 | 11.0 | 6.8 | 7.8 |
| Year 11 | 5.1 | 7.0 | 6.5 | 6.3 |
| Total Yield | 8.7 | 18.0 | 13.3 | 14.1 |
| Fruit weight (g) | | | | |
| Year 10 | 4.30 | 4.16 | 3.10 | 3.06 |
| Year 11 | 3.84 | 3.54 | 3.19 | 3.37 |
| Fruit firmness (g) | | | | |
| Year 10 | 101 | 90 | 74 | 74 |
| Year 11 | 137 | 107 | 106 | 122 |
| Fruit rot (%) | | | | |
| Year 10 | 4.4 | 9.8 | 11.4 | 7.2 |
| Year 11 | 5.4 | 14.5 | 10.6 | 6.6 |
| Date of first harvest | | | | |
| Year 10 | 6/14 | 6/13 | 6/16 | 6/12 |
| Year 11 | 6/22 | 6/28 | 6/28 | 6/22 |
| Midpoint of harvest | | | | |
| Year 10 | 6/19 | 6/23 | 6/28 | 6/19 |
| Year 11 | 7/8 | 7/12 | 7/9 | 7/6 |
| Date of last harvest | | | | |
| Year 10 | 7/6 | 7/13 | 7/14 | 7/6 |
| Year 11 | 7/21 | 7/27 | 7/27 | 7/20 |

[Z]Harvest of non-replicated 8 plant plots.
[Y]Harvest of 3 replications of 3 plants.

Table 2 provides information on the plant and fruit characteristics of the new variety 'WSU 2166'. The table compares 'WSU 2166' with 'Cascade Harvest' and 'Meeker', both varieties grown commercially in Washington.

TABLE 2

Measurements of plant characteristics.

| | 'WSU 2166' | 'Cascade Harvest' | 'Meeker' |
|---|---|---|---|
| Plant height (m) | 2.08 | 1.91 | 1.91 |
| Plant width (m) | 1.32 | 1.09 | 1.35 |
| Self-fertile | yes | yes | yes |
| Flower-measurements[x] | | | |
| Date of first bloom | 5/7 | 5/9 | 5/10 |
| Length of bloom (days) | 29 | 28 | 31 |
| Number of petals | 5 | 5 | 5 |
| Length of petal (mm) | 8.09 | 6.09 | 6.01 |
| Width of petal (mm) | 3.59 | 3.50 | 4.13 |
| Color petal upper surface (RHS) | White NN155D | White NN155D | White NN155D |
| Color petal lower surface (RHS) | White NN155D | White NN155D | White NN155D |
| Petal shape | Oblanceolate | Oblanceolate | Oblanceolate |
| Petal margin | Entire | Entire | Entire |
| Flower diameter petal tip to petal tip at widest part of the flower (mm) | 17.9 | 17.9 | 17.8 |
| Number of sepals | 5 | 5 | 5 |
| Color sepal upper surface (Munsell) | 5GY 7/6 | 5GY 7/6 | 7.5GY 7/6 |
| Color sepal lower surface (Munsell) | 5GY 7/8 | 5GY 7/8 | 5GY 7/6 |
| Length of sepal (mm) | 7.25 | 6.93 | 7.56 |
| Width of sepal (mm) | 5.70 | 5.55 | 5.40 |
| Flower diameter sepal tip to sepal tip at the widest part of the flower (mm) | 21.0 | 21.0 | 20.8 |
| Number of stigma/flower | 58 | 73 | 61 |
| Number of anthers/flower | 82 | 92 | 65 |
| Flower fragrance | none noted | none noted | none noted |
| Fruit Measurements | | | |
| Fruit color (Munsell) | 4.4R 2.6/5.1 | 5.8R 2.5/4.9 | 5.1R 2.6/5.1 |
| Fruit weight (g) | 4.6 | 5.7 | 3.8 |
| Fruit length (mm) | 26.4 | 28.4 | 21.7 |
| Fruit width (mm) | 21.0 | 22.3 | 20.0 |
| Fruit length/width ratio | 1.26 | 1.27 | 1.09 |
| Pedicle length (mm) | 24.4 | 27.8 | 16.2 |
| Receptacle length (mm) | 21.7 | 22.0 | 16.8 |
| Receptacle width (mm) | 8.8 | 8.9 | 9.0 |
| Drupelet length (mm) | 5.0 | 5.2 | 5.1 |
| Drupelet width (mm) | 4.3 | 4.5 | 3.7 |
| Drupelet weight (mg) | 42.0 | 51.1 | 33.1 |
| Number of seeds per fruit | 110.2 | 111.8 | 113.8 |
| Seed weight (mg) | 1.75 | 1.95 | 1.70 |
| Primocanes | | | |
| Number of primocanes/hill | 11.7 | 25.7 | 18.1 |
| Length of primocane (m) | 2.34 | 2.19 | 2.55 |
| Diameter at ground (mm) | 9.9 | 11.5 | 1.19 |
| Diameter at 1.2 m (mm) | 8.6 | 9.8 | 8.8 |
| Number of nodes | 43 | 43 | 50 |
| Internode length at 1.2 m (cm) | 9.0 | 11.2 | 7.5 |
| Color primocane spines (RHS) | 59C | 187A | 187A |
| Length spine (mm) | 1.6 | 2.3 | 1.5 |
| Length base of spine (mm) | 2.6 | 2.9 | 1.4 |
| Width base of spine (mm) | 1.5 | 1.4 | 0.9 |
| Color spine base (RHS) | 187A | 187A | 59C |
| Primary cane color (Munsell) | 2.6GY 6.9/3.9 | 1.3GY 6.5/3.9 | 2.2GY 6.6/4.0 |
| Secondary cane color (Munsell) | 7.9R 3.9/4.5 | 6.6R 3.8/4.8 | 7.9R 3.9/4.5 |
| Primocane fruiting | no | no | no |
| Pubescence on canes | absent | absent | slight |
| Floricanes | | | |
| Primary cane color (Munsell) | 2.6GY 6.9/3.9 | 1.3GY 6.5/3.9 | 2.2GY 6.6/4.0 |

TABLE 2-continued

Measurements of plant characteristics.

| | 'WSU 2166' | 'Cascade Harvest' | 'Meeker' |
|---|---|---|---|
| Secondary cane color (Munsell) | 7.9R 3.9/4.5 | 6.6R 3.8/4.8 | 7.9R 3.9/4.5 |
| Primocane fruiting | no | no | no |
| Pubescence on canes | absent | absent | slight |
| Number of floricanes/hill | 8.0 | 10.0 | 10.0 |
| Diameter at base (mm) | 12.5 | 9.8 | 11.4 |
| Diameter at 1.2 m (mm) | 9.6 | 7.6 | 11.1 |
| Internode length at 1.2 m (cm) | 7.1 | 6.6 | 6.9 |
| Height (m) | 1.7 | 1.7 | 1.7 |
| Lateral length 1.2 m (cm) | 161 | 146 | 140 |
| Nodes/lateral | 16.0 | 11.3 | 12.7 |
| Number fruit/lateral | 17.3 | 21.0 | 15.0 |
| Number fruit/fruiting node | 1.8 | 3.7 | 2.1 |
| Color primocane leaves[z] | | | |
| Upper surface (Munsell) | 6.3GY 4.2/5.3 | 6.3GY 3.8/4.6 | 6.5GY 3.7/4.4 |
| Lower surface (Munsell) | 6.3GY 5.6/2.9 | 6.2GY 5.2/3.0 | 6.1GY 5.5/2.2 |
| Color floricane leaves[y] | | | |
| Upper surface (Munsell) | 5.6GY 4.1/5.2 | 6.1GY 3.7/5.0 | 6.1GY 3.9/5.1 |
| Lower surface (Munsell) | 5.6GY 5.3/2.9 | 5.9GY 5.3/2.8 | 6.0GY 5.5/2.5 |
| Primocane leaves | | | |
| Number of leaflets | 5 | 5 | 5 |
| Petiole length (mm) | 88.9 | 98.9 | 88.7 |
| Rachis length (mm) | 45.8 | 51.1 | 40.8 |
| Stipule (mm) | 6.3 | 8.3 | 11.3 |
| Leaflet margins | doubly serrated | doubly serrated | doubly serrated |
| Leaflet overlap | occasionally overlap | occasionally overlap | commonly overlap |
| Terminal leaflet | | | |
| Length (mm) | 114.0 | 103.9 | 102.5 |
| Width (mm) | 75.8 | 67.0 | 68.2 |
| Length/width | 1.5 | 1.5 | 1.5 |
| Leaflet tip | cuspidate | cuspidate | cuspidate |
| Leaflet base | oblique | cordate | obtuse |
| Distal lateral leaflet | | | |
| Length (mm) | 77.1 | 83.2 | 78.4 |
| Width (mm) | 57.4 | 41.6 | 39.2 |
| Length/width | 1.6 | 1.6 | 1.6 |
| Petiolule length (mm) | 1.6 | 1.6 | 1.6 |
| Leaflet tip | cuspidate | cuspidate | cuspidate |
| Leaflet base | obtuse | oblique | oblique |
| Basal leaflet | | | |
| Length (mm) | 93.2 | 94.6 | 98.2 |
| Width (mm) | 57.4 | 58.8 | 60.0 |
| Length/width | 1.6 | 1.6 | 1.6 |
| Petiolule length (mm) | 1.7 | 3.4 | 3.8 |
| Leaflet tip | cuspidate | cuspidate | cuspidate |
| Leaflet base | obtuse | oblique | oblique |
| Floricane leaves | | | |
| Leaflet number | 3 | 3 | 3 |
| Petiole (mm) | 53.0 | 46.8 | 53.1 |
| Leaflet margins | doubly serrated | doubly serrated | doubly serrated |
| Terminal leaflet | | | |
| Length (mm) | 93.8 | 87.4 | 93.2 |
| Width (mm) | 70.0 | 80.4 | 61.4 |
| Length/width | 1.4 | 1.1 | 1.5 |
| Petiolule (mm) | 25.4 | 30.2 | 24.5 |

TABLE 2-continued

Measurements of plant characteristics.

| | 'WSU 2166' | 'Cascade Harvest' | 'Meeker' |
|---|---|---|---|
| Basal leaflet | | | |
| Length (mm) | 82.9 | 78.1 | 75.5 |
| Width (mm) | 49.1 | 48.1 | 43.2 |
| Length/width | 1.7 | 1.6 | 1.8 |
| Petiolule (mm) | 1.9 | 2.8 | 2.0 |

[X]Flower measurements made in Year 13.

[Z]The leaf color of the upper surface of the primocane terminal leaflet, distal leaflets and the basal leaflets did not vary among leaflets of the primocane leaf. The leaf color of the lower surface of the primocane terminal leaflet, distal leaflets and the basal leaflets did not vary among leaflets of the primocane leaf.

[Y]The leaf color of the upper surface of the floricane terminal leaflet and the basal leaflets did not vary among leaflets of the primocane leaf. The leaf color of the lower surface of the floricane terminal leaflet and the basal leaflets did not vary among leaflets of the primocane leaf.

Machine harvested fruit was collected in Lynden, Wash. in Year 7. 'WSU 2166' had slightly higher titratable acidity and lower pH than 'Meeker' and 'Willamette', resulting in a slightly more tart flavor. Table 3 provides the comparative values for anthocyanin content, soluble solids, pH and titratable acidity of raspberry fruit for the 'WSU 2166', 'Meeker' and 'Willamette' varietals.

TABLE 3

Anthocyanin content, soluble solids, pH and titratable acidity of raspberry fruit machine harvested in Year 7 at Lynden, WA. Based on fruit samples of approximately 300 g collected for each cultivar.

| | 'WSU 2166' | 'Meeker' | 'Willamette' |
|---|---|---|---|
| Soluble solids (deg. Brix) | 8.2 | 9.3 | 8.0 |
| pH | 3.31 | 3.54 | 3.34 |
| Titratable acidity (% citric acid) | 2.00 | 1.40 | 1.83 |
| Total anthocyanins (mg C-3-G/100 g FW) | 52 | 57 | 95 |

[Z]Acidity expressed as % citric acid.

[X]Total anthocyanins determined spectrophotometrically from acidified ethanol extracts and expressed as cyanidin-3-galactoside.

Table 4 provides the root rot evaluation of 'WSU 2166', 'Cascade Harvest' and 'Meeker', which were evaluated for susceptibility to root rot in plots at Puyallup, Wash. in plantings established in Year 8. The presence of *Phytophthora fragariae* var *rubi* ([W. F. Wilcox & J. M. Duncan] W. A. Man in't Veld,) in these root rot plots has been verified via PCR. Four plants of each clone were planted in this area. Plants were subjectively rated for vigor in the fall of each year from 0 to 5, with 0 being dead and 5 a healthy and vigorous plant. Year 11 was a very severe root rot test. Other raspberries in the same planting had a decrease in their vigor ratings by an average of over 40% from Year 10 to Year 11. In the fall of the fourth year, 'WSU 2166' plants had a rating of 3.5, while 'Meeker' averaged 2.5 and 'Cascade Harvest' averaged 1.0. Based on this trial, 'WSU 2166' demonstrates a relatively high root rot tolerance, although it is not absolutely unaffected.

TABLE 4

Root rot evaluation

| Date | 'WSU 2166' | 'Cascade Harvest' | 'Meeker' |
|---|---|---|---|
| Nov. 6, 2015 | 2.50 | 4.25 | 4.00 |
| Nov. 4, 2016 | 4.50 | 5.00 | 4.75 |
| Sep. 13, 2017 | 3.50 | 1.00 | 2.50 |

Four plants of each cultivar planted in Year 8 Subjectively rated 0-5. 0=dead, 5=healthy and vigorous.

'WSU 2166' was planted in non-replicated plots with cooperating growers in Year 5 and Year 8. The plantings were maintained by growers using typical commercial methods and the fruit machine harvested. The plantings were subjectively evaluated for adaptation to machine harvesting weekly during the harvest season for two fruiting seasons. In all harvest seasons 'WSU 2166' machine harvested well and was productive with large fruit size. Based on these evaluations, 'WSU 2166' is suitable for machine harvesting.

What is claimed:

1. A new and distinct variety of raspberry plant, as illustrated and described herein.

* * * * *